United States Patent
Van Erp

[11] Patent Number: 5,591,142
[45] Date of Patent: Jan. 7, 1997

[54] CATHETER WITH WIRE REINFORCEMENT HAVING GOOD ELECTRICAL CONDUCTIVITY

[75] Inventor: Wilhelmus P. M. M. Van Erp, Leek, Netherlands

[73] Assignee: Cordis Corporation, Miami Lakes, Fla.

[21] Appl. No.: 428,506

[22] Filed: Apr. 25, 1995

Related U.S. Application Data

[63] Continuation of Ser. No. 230,400, Apr. 20, 1994, abandoned.

[30] Foreign Application Priority Data

Apr. 20, 1993 [NL] Netherlands ............ 9300670

[51] Int. Cl.$^6$ ............................................ A61M 25/00
[52] U.S. Cl. ........................ 604/282; 604/264; 607/122
[58] Field of Search ........................ 604/20, 21, 264, 604/280, 282; 607/115, 116, 122

[56] References Cited

U.S. PATENT DOCUMENTS

| | | | |
|---|---|---|---|
| 4,050,411 | 9/1977 | Kimmich | 118/625 |
| 4,073,287 | 2/1978 | Bradley et al. | 604/21 X |
| 4,176,662 | 12/1979 | Frazer | 604/21 X |
| 4,665,604 | 5/1987 | Dubowik . | |
| 4,776,334 | 10/1988 | Prionas . | |
| 4,840,186 | 6/1989 | Lekholm et al. | 607/116 |
| 4,945,342 | 7/1990 | Steinemann | 607/116 X |
| 4,947,866 | 8/1990 | Lessar et al. | 607/116 |
| 5,279,596 | 1/1994 | Castaneda et al. | 604/282 |
| 5,290,230 | 3/1994 | Ainsworth et al. . | |
| 5,324,275 | 6/1994 | Raad et al. | 604/265 |
| 5,334,169 | 8/1994 | Brown et al. . | |

FOREIGN PATENT DOCUMENTS

| | | |
|---|---|---|
| 0249338 | 12/1987 | European Pat. Off. . |
| 2218580 | 11/1989 | United Kingdom . |

*Primary Examiner*—Corrine M. McDermott
*Attorney, Agent, or Firm*—Thomas R. Vigil

[57] ABSTRACT

The catheter comprises a generally tubular, thin walled body having a metal wire reinforcing layer defined by metal wires which are woven or wound into a generally cylindrical weave of metal wire reinforcement incorporated into the tubular body. The catheter has a distal end portion and a proximal end portion. The catheter also has at least one lumen within the tubular body. At least one electrical operating element, such as an electrically conductive sensor, is mounted on the distal end portion and is electrically connected to at least one of the wires. An electrical connecting member is mounted on the proximal end portion and electrically connected to at least one of the wires. The metal wires include at least two bundles of wires in each of which the wires are arranged side by side to enable the tubular body to have a very thin wall and are made of material, such as phosphor bronze, and not stainless steel, that will provide wires which have sufficiently high mechanical strength to impart torque transmitting properties to the catheter and which also have good electrical conductivity.

12 Claims, 2 Drawing Sheets

CATHETER WITH WIRE REINFORCEMENT HAVING GOOD ELECTRICAL CONDUCTIVITY

This is a continuation of application Ser. No. 08/230,400 filed on Apr. 20, 1994, now abandoned.

BACKGROUND OF THE INVENTION

1. Field Of The Invention

The present invention relates to a catheter comprising a generally tubular, thin walled body with a woven or wound round metal wire reinforcement. Such catheters are known, for instance, as angiographic catheters. The metal wire reinforcement serves to give the catheter a great torsional rigidity and pressure resistance at a small diameter. Because the catheter can resist a high pressure, a sufficient quantity of liquid, such as contrast fluid, can be transported in the catheter to the desired position in the bloodstream of a patient even when the diameter of the lumen is small. Such delivery can be through a distal outlet port as disclosed in the Spector et al. E.P. Publication No. 0 249 338.

2. Description Of The Related Art

Heretofore various metal wire reinforced catheters have been proposed and analogous and non-analogous examples of some of these catheters are disclosed in the following U.S. Patents and foreign patent publications:

| U.S. Pat. No. | Patentee |
|---|---|
| 4,050,411 | Kimmich |
| 4,073,287 | Bradely et al. |
| 4,176,662 | Frazer |
| 4,406,656 | Hattler et al. |
| 4,572,186 | Gould et al. |
| 4,665,604 | Dubowik |
| 4,776,334 | Prionas |
| 4,840,186 | Lekholm et al. |
| 4,945,342 | Steinemann |
| 4,947,866 | Lessar et al. |
| 5,279,596 | Castaneda et al. |
| 5,290,230 | Ainsworth et al. |
| 5,324,275 | Raad et al. |
| 5,334,169 | Brown et al. |
| British Published Patent Application | |
| UK Patent Appl. No. 2,218,580 to Nogami at al. | |
| EP Published Patent Application | |
| EP Pub. No. 0 249 338 to Spector et al | |

SUMMARY OF THE INVENTION

The invention has for its objective to provide a new metal wire reinforced catheter.

According to the present invention there is provided a catheter comprising a generally tubular, thin walled body having therein a metal wire reinforcement layer defined by metal wires which are woven or wound into a generally cylindrical weave and incorporated into the catheter, the catheter having a distal end portion and a proximal end portion, at least one electrical operating element, such as an electrically conductive sensor, being mounted on the distal end portion and electrically connected to at least one of the wires, and an electrical connecting member being mounted on the proximal end portion and electrically connected to at least one of the wires, the metal wires including at least two bundles of wires in each of which the wires are arranged side by side to enable said tubular body to have a very thin wall and being made of a strong, but conductive material, like phosphor bronze, and not stainless steel, to provide metal wires which have sufficiently high mechanical strength to impart torque transmitting properties to the catheter and which also have good electrical conductivity.

The metal wire reinforcement, or at least one or more wires thereof, are used as an electrical conductor so that no separate electrical conductors have to be incorporated in the catheter and the catheter can thus retain a small diameter.

In one suitable embodiment of a catheter, constructed according to the teachings of the present invention, the metal wire reinforcement is uncoated and is manufactured from uncoated wires and connected to the connecting member. The woven or wound metal wire reinforcement can function in this embodiment as an earth lead or shielding protector, much like a coaxial cable. Then, through the lumen of the catheter, one can arrange, for instance, a high-frequency conductor which conducts energy to the distal end of the catheter without the intermediate region being affected in an undesired manner.

In another embodiment, the metal wire reinforcement is manufactured from separately insulated metal wires which are separately connected to electrically operating elements and connecting members therefor. Each of the separately insulated metal wires can thus form a conductor, for instance, for a sensor on the distal end of the catheter. Since it is usual to employ a comparatively large number of wires in a metal wire reinforcement, a typical number being, for instance, 16, a large number of different signal currents or other electrical currents can be conducted between the distal and the proximal end of the conductor without the catheter having to be given a larger diameter to receive the conductors.

Another favorable feature is the coding of the separately insulated metal wires to provide easy visual recognition of one or more of the wires.

It is also possible to color code the separately insulated metal wires in a simple color code manner to enable one to make the correct connections at the one end of the catheter as well as at the other end. When the wires of the metal wire reinforcement are released at one end of the catheter it is very simple to see which wire belongs to which connection at the other end by means of the color coding.

According to the invention, phosphor bronze wires are used for the metal wires of the metal wire reinforcement. Compared to the usual stainless steel or other sufficient mechanically supportive and electrically conductive material, phosphor bronze has the advantage of a good electrical conductivity so that little loss occurs. Phosphor bronze has high strength so that the choice of this material does not have an unfavorable effect on the further properties of the catheter.

The catheter with a metal reinforcement is further explained in the following description with reference to the drawings.

DESCRIPTION OF THE PREFERRED EMBODIMENTS

Figure 1:
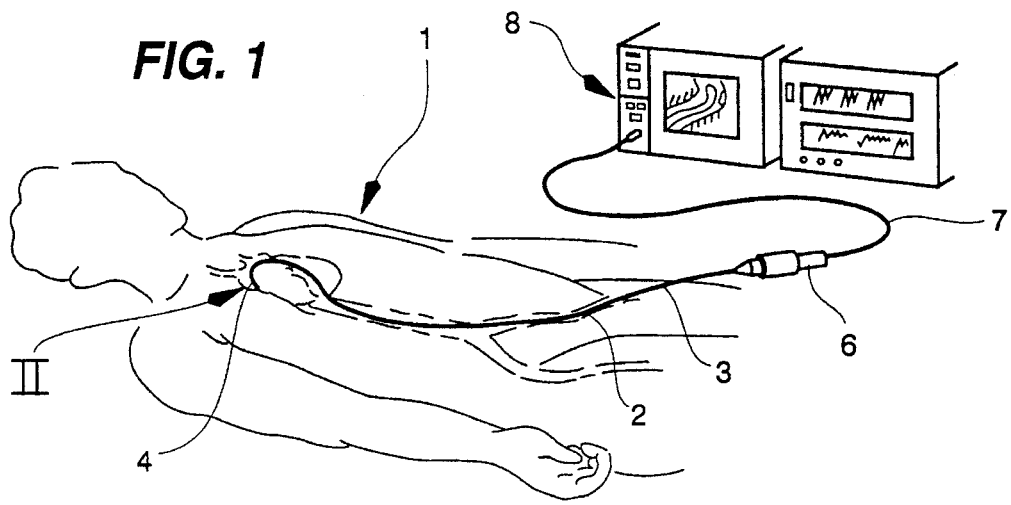
FIG. 1 shows schematically the use of a catheter constructed according to the teachings of the present invention.

Designated in FIG. 1 with the reference numeral 1 is a patient, in whom a test in the blood circulatory system is being performed. Introduced into a blood vessel 2 of the patient 1 is a catheter 3 constructed according to the teachings of the present invention wherein at least one electrically operating element, such as a sensor 5, is arranged on the distal end 4. Liquid, such as contrast fluid can be transported by the catheter 3 to a desired position in the blood stream. If desired, the distal end 4 can have a distal outlet port for delivering the fluid as disclosed in the Spector et al. E.P. Publication No. 0 249 338, the disclosure of which is incorporated herein by reference. On the proximal end of catheter 3 is a connecting member 5A. The electrically operating element, such as the sensor 5, is connected via one or more metal wires (wires 11 shown in FIG'S. 3 and 4) of a metal wire reinforcement (wire reinforcement 15 shown in FIG'S. 3 and 5) woven or wound around the catheter 3 and connected to the connecting member 5A of the catheter 3. By means of an electrical conductor 7 with a coupling 6, a connection can be effected from the connecting member 5A to a processing device 8 which processes the signals from the electrical operating element 5 at the distal end 4 of the catheter 3.

Figure 2A:
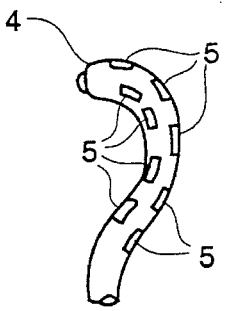
FIG. 2A and 2B show schematically the outer end of catheters according to an embodiment of the invention.
Figure 2B:
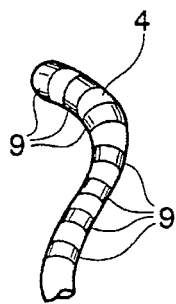

As shown schematically in FIG. 2A and 2B, the distal end 4 can carry a number of electrically operating elements, such as sensors 5 and 9. These sensors may, for instance, be the sensitive or guide sensors.

Figure 4:
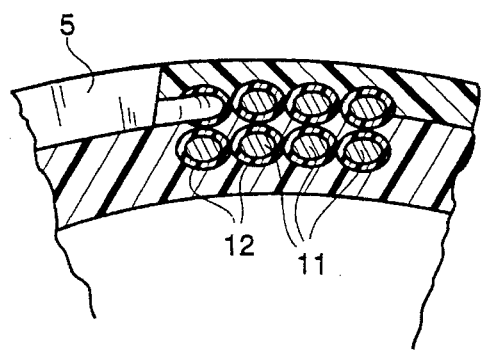
FIG. 4 shows a partial section along IV—IV in FIG. 3.

As shown in more detail in FIG. 4, each of the sensors is connected to one of the wires 11 of wire bundles 10.

In another embodiment, the reinforcing may be formed by separate wires instead of by wire bundles.

Figure 5:
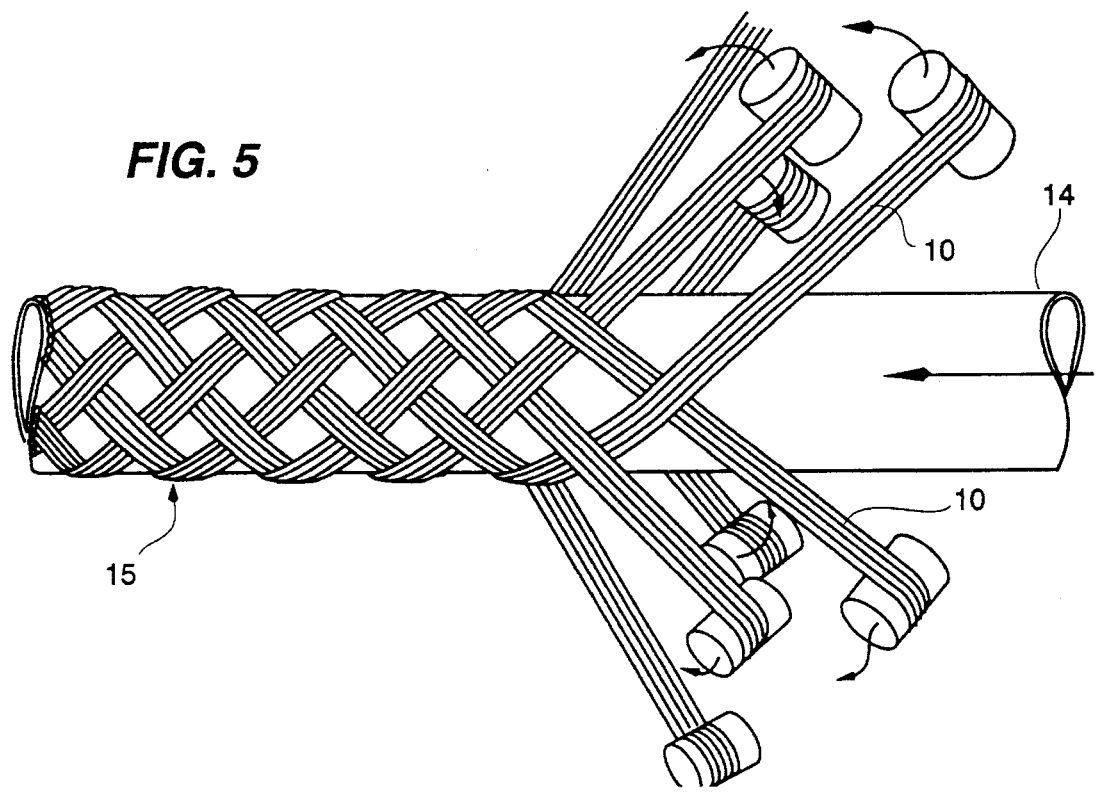
FIG. 5 shows schematically the production of the basic body material for a catheter according to the invention.

The construction of the basic body of the catheter 3 is per se known and generally comprises a base tubular layer 14, a woven metal wire reinforcing layer 15 forming a generally cylindrical weave of reinforcing wires 11 and a coating layer 16 arranged thereover. As FIG. 5 shows, the wire bundles 10 are woven or wound around the base layer 14 with the metal wires 11 arranged side by side, as shown in FIG'S 3, 4 and 5, to form the reinforcing layer 15. The coating 16 is arranged thereover afterwards. Reinforcing layer 15 may also be formed of wound metal wires. The basic tubular body of the catheter 3 may alternatively be formed with a reinforcing layer without a base layer and a coating layer, the reinforcing layer being incorporated into the catheter 3, i.e., in a manner similar to the embedding of a braided stainless steel wire in a catheter base strand as disclosed in the Dubowik U.S. Pat. No. 4,665,604, the disclosure of which is incorporated herein by reference. The side by side arrangement of the metal wires 11 in each bundle 10 with no single wire in a bundle overlying another single wire in the bundle enables the tubular body of the catheter 3 to have a very thin wall.

As shown in FIG. 4 in more detail, each of the wires 11 of the wire bundles 10, in the shown embodiment of the catheter 3, is provided with its own insulating layer 12. Each of the wires 11 can then be used as a separate conductor for carrying electrical currents from the one end of the catheter to the other.

As shown in FIG. 4, the metal wires are grouped into two or more bundles, namely eight bundles, which are cross woven diagonally around the base layer 14 of the catheter 3.

Figure 4A:
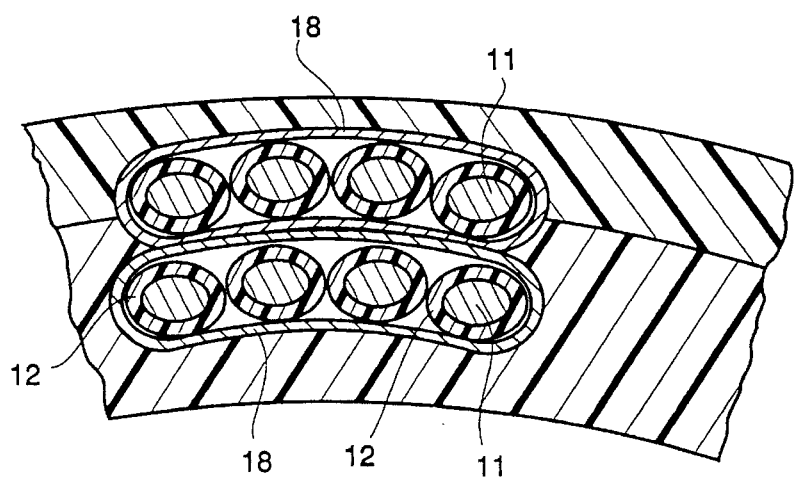
FIG. 4A is a sectional view similar to FIG. 4 but shows a metal layer around the insulated wires of the metal wire reinforcement of the catheter shown in FIG. 3.

Another possibility is to provide each conducting wire with its own insulating layer 12 and to arrange yet another metal layer 18 therearound, as shown in FIG. 4A. The character of a shielded cable is thus obtained. With such a catheter, low level measurement signals can, for instance, be reliably transported in suitable manner from a sensor on the distal end to a processing device at the proximal end.

In the production method shown schematically in FIG. 5, eight wire bundles of four wires are used so that in principle thirty-two conductors are formed.

In an embodiment of the catheter, according to the invention wherein the wires are indeed used as separate conductors, the different wires 11 are individually coded for visual recognition, for instance, using a color code. In this way, it is simple to identify at the one end of the catheter which wire is connected in a particular manner at the other end.

Instead of a sensor, the electrically operating element at the distal end of the catheter can also be an interventional element, such a heat-generating element or the like.

Instead of recognition coding of separate wires, the bundles 10 can also be coded for visual recognition. The position of the separate wires 11 in the bundles 10 makes it possible to identify the separate wires. It is also possible to jointly insulate all wires 11 in a bundle 10 and to use these wires as one conductor.

Figure 3:
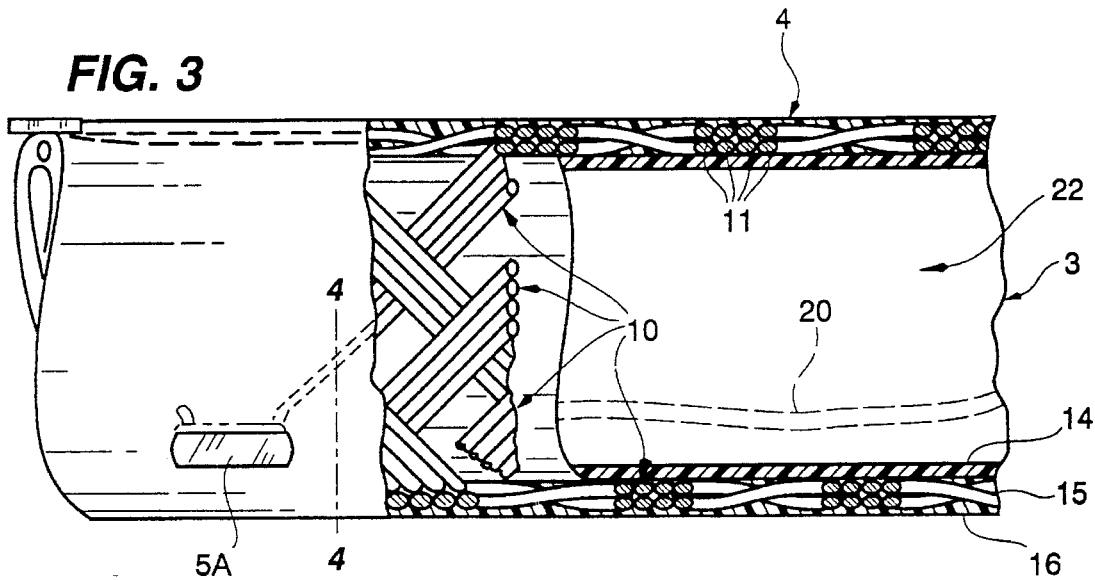
FIG. 3 shows a partly broken away view on a larger scale the catheter end portion of FIG. 2A.

In an application wherein the wires are not insulated, the whole metal wire reinforcement can function as one conductor, for instance, as earthed shielding for a high-frequency energy-carrying conductor 20 received in the lumen 22 of the catheter 3, as shown in phantom in FIG. 3.

As noted above, phosphor bronze is a suitable and desired metal for the wires 11 of the catheter 3 according to the invention. Phosphor bronze has a mechanically high strength and a good electrical conductivity so that wires of this material can provide the catheter with the desired mechanical and electrical properties.

I claim:

1. A catheter comprising a generally tubular body having a metal wire reinforcing layer defined by metal wires which are woven into a cylindrical weave of metal wire reinforcement incorporated into said catheter, said catheter having a distal end portion, a proximal end portion and at least one lumen in said catheter, at least one electrical operating element being mounted on said distal end portion and electrically connected to at least one of said wires, and an electrical connecting member being mounted on said proximal end portion and electrically connected to at least one of said wires, said metal wires including at least two bundles of single wires, the single wires in each bundle being arranged side by side with no single wire in a bundle overlying another single wire in said bundle to enable said tubular body to have a very thin wall and each single wire being made of a material which has sufficiently high mechanical strength to impart torque transmitting properties to said catheter and which also has good electrical conductivity.

2. A catheter as claimed in claim 1, wherein said metal wire reinforcement is uncoated and is manufactured from uncoated wires which are connected to said connecting member.

3. A catheter as claimed in claim 1, wherein said metal wire reinforcement is manufactured from separately insulated metal wires which are separately connected to electrical operating elements and connecting members therefor.

4. A catheter as claimed in claim 3, wherein the separately insulated metal wires are coded for visual recognition.

5. A catheter as claimed in claim 4, wherein the separately insulated metal wires carry a color coding.

6. A catheter as claimed in claim 1 wherein said tubular body comprises: (a) a base tubular layer, (b) said metal wire reinforcing layer which is woven around said base tubular layer and (c) a coating layer over said woven metal wire reinforcing layer, thereby to provide a thin walled catheter.

7. A catheter as claimed in claim 1 further comprising a high-frequency energy-carrying conductor received within said lumen in said catheter and wherein said metal wires are not insulated from each other so that said metal wire reinforcement forms a shielded cable for said high-frequency energy-carrying conductor received in said lumen.

8. A catheter as claimed in claim 1 wherein said metal wires comprise eight wire bundles of four wires each so that thirty-two wire conductors are woven into the cylindrical weave.

9. A catheter as claimed in claim 1 having an outlet opening whereby liquid can be transported in said catheter to a desired position in a patient's bloodstream.

10. A catheter as claimed in claim 1 wherein said metal wires are grouped into two or more bundles which are cross woven diagonally around said body of said catheter.

11. A catheter comprising a generally tubular body having a metal wire reinforcing layer defined by single metal wires which are woven into a cylindrical weave of metal wire reinforcement and incorporated into said catheter, said catheter having a distal end portion, a proximal end portion, at least one electrical operating element being mounted on said distal end portion and electrically connected to at least one of said wires, an electrical connecting member being mounted on said proximal end portion and electrically connected to at least one of said wires, said metal wires having sufficiently high mechanical strength to impart torque transmitting properties to said catheter and having good electrical conductivity, each conducting wire of said metal wire reinforcement having its own insulating layer and a metal layer surrounding a bundle of said single wires thereby to provide a shielded cable whereby, with said catheter, low level measurement signals can be reliably transported by said metal wire reinforcement in a suitable manner from said electrical operating element on said distal end portion to a processing device connected to said electrical connecting member on said proximal end portion.

12. A catheter comprising a generally tubular body having a metal wire reinforcing layer defined by metal wires which are woven into a cylindrical weave of metal wire reinforcement incorporated into said catheter, said catheter having a distal end portion, a proximal end portion and at least one lumen in said catheter, at least one electrical operating element being mounted on said distal end portion and electrically connected to at least one of said wires, and an electrical connecting member being mounted on said proximal end portion and electrically connected to at least one of said wires, said metal wires including at least two bundles of wires, in each of which the wires are arranged side by side to enable said tubular body to have a very thin wall and being made of phosphor bronze, a material which has sufficiently high mechanical strength to impart torque transmitting properties to said catheter and which also has good electrical conductivity.

* * * * *